United States Patent [19]
Johnson et al.

[11] 4,146,022
[45] Mar. 27, 1979

[54] FRACTURE FIXATION BY CERCLAGE UTILIZING CORTICAL BONE TACK AND PULL-OUT TENSION DEVICE

[75] Inventors: Ronald A. Johnson, Oakland Hospital for Animals, Inc., 2200 W. Oakland Park Blvd., Ft. Lauderdale, Fla. 33311; Horst R. Hickmann, Cincinnati, Ohio

[73] Assignee: Ronald A. Johnson, Ft. Lauderdale, Fla.

[21] Appl. No.: 851,837

[22] Filed: Nov. 16, 1977

[51] Int. Cl.² .................... A61F 5/04; A61B 17/18
[52] U.S. Cl. ........................... 128/92 B; 128/92 BC; 128/92 EA; 128/321
[58] Field of Search ............. 128/92 B, 92 BC, 92 D, 128/92 E, 92 EA, 92 G, 83, 321, 346

[56] References Cited
U.S. PATENT DOCUMENTS

| | | | |
|---|---|---|---|
| 2,291,413 | 7/1942 | Siebrandt | 128/92 EA X |
| 2,583,896 | 1/1952 | Siebrandt | 128/92 EA X |
| 3,111,945 | 11/1963 | Von Solbrig | 128/92 EA |
| 3,270,745 | 9/1966 | Wood | 128/346 X |
| 3,469,573 | 9/1969 | Florio | 128/92 B |
| 3,477,429 | 11/1969 | Sampson | 128/92 R |
| 3,709,218 | 1/1973 | Halloran | 128/92 BC X |
| 4,047,524 | 9/1977 | Hall | 128/92 B |

OTHER PUBLICATIONS

Mario M. Stone, Table Staple, Richards Mfg. Co., Orthopedic and Instruments (catalog), Memphis, Tenn., 1966, p. 115.

*Primary Examiner*—Ronald L. Frinks
*Attorney, Agent, or Firm*—Melville, Strasser, Foster & Hoffman

[57] ABSTRACT

An orthopedic implant for use in the internal fixation of a bone fracture by wiring, a method of fracture fixation by wiring which avoids bone resorption, and means for embedding the implant in the cortex of a bone adjacent the fracture site. The implant comprises a cylindrical body portion, a plurality of pointed pins at one end of the body portion, a circular bore through the body portion through which a wire may be passed, and at least one groove on the surface of the body portion in which a wire may be accommodated.

14 Claims, 23 Drawing Figures

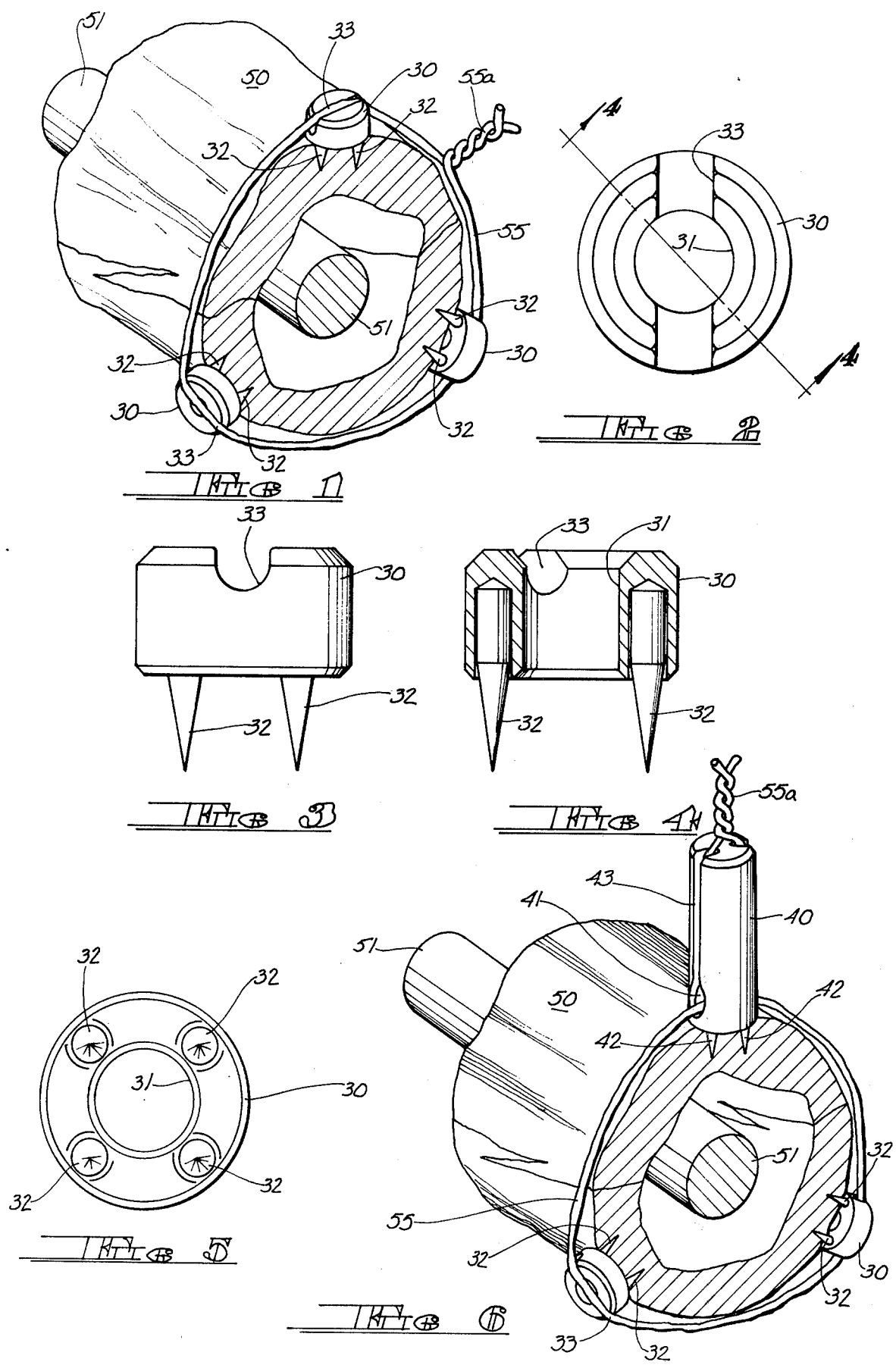

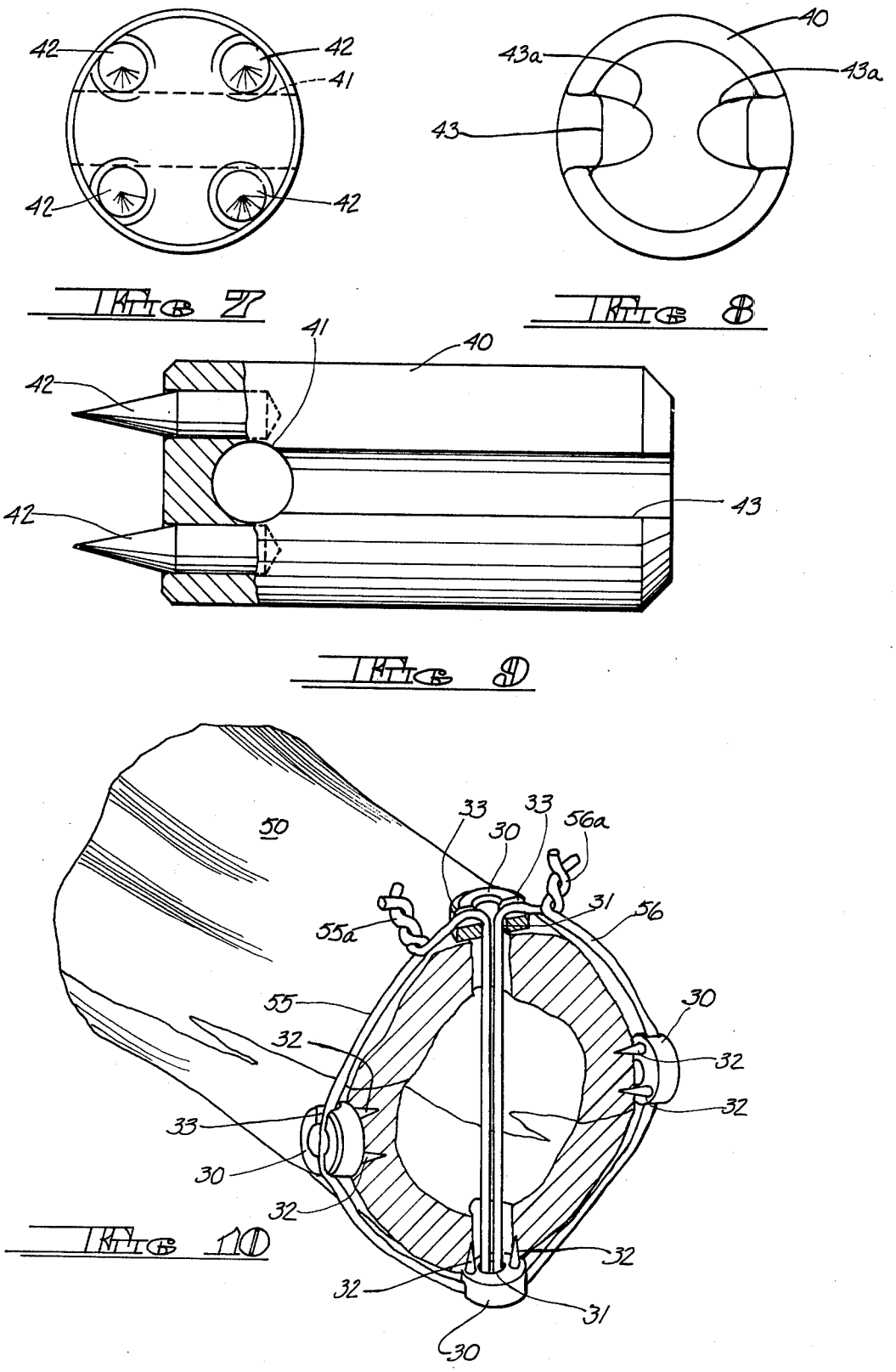

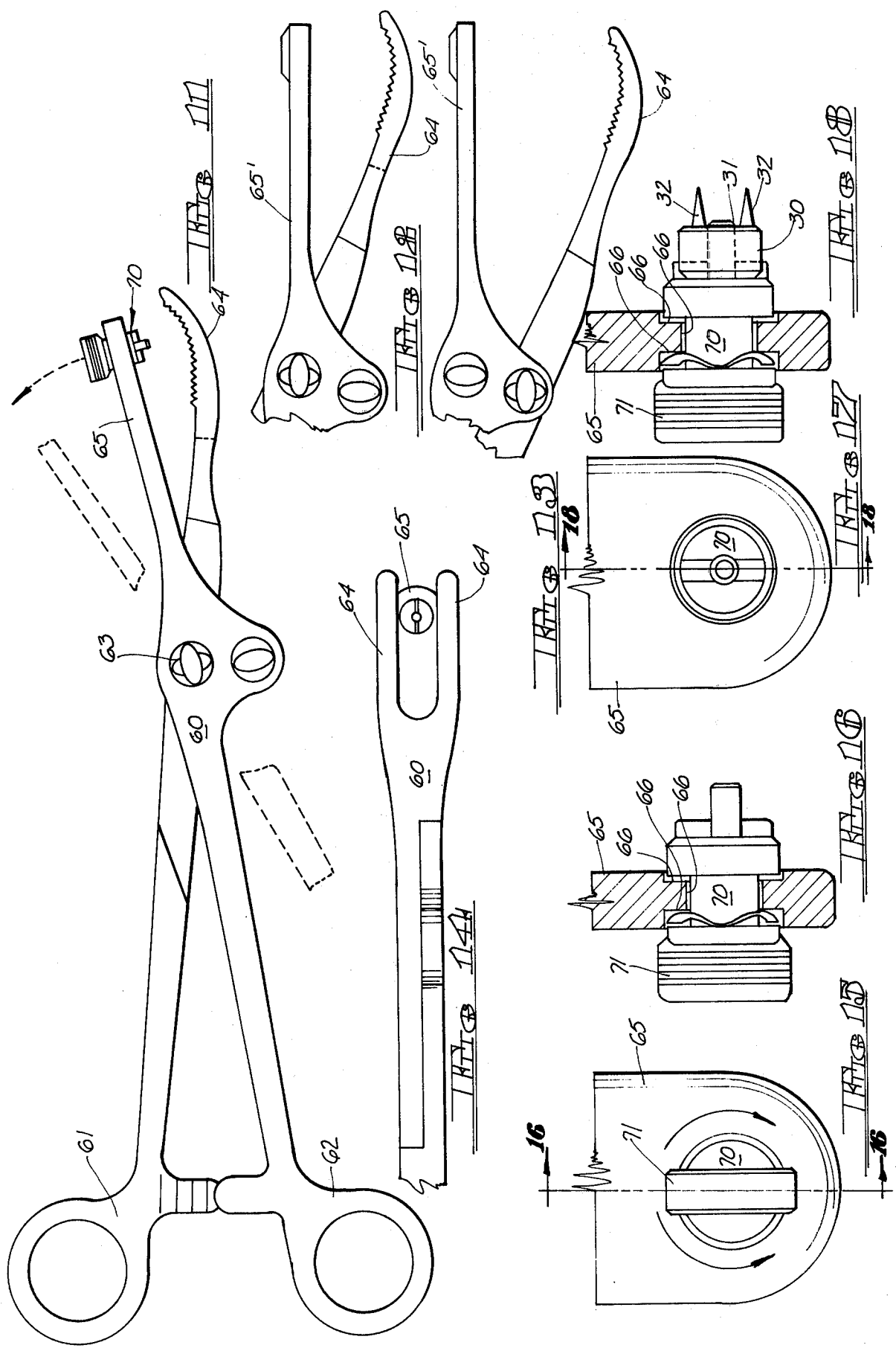

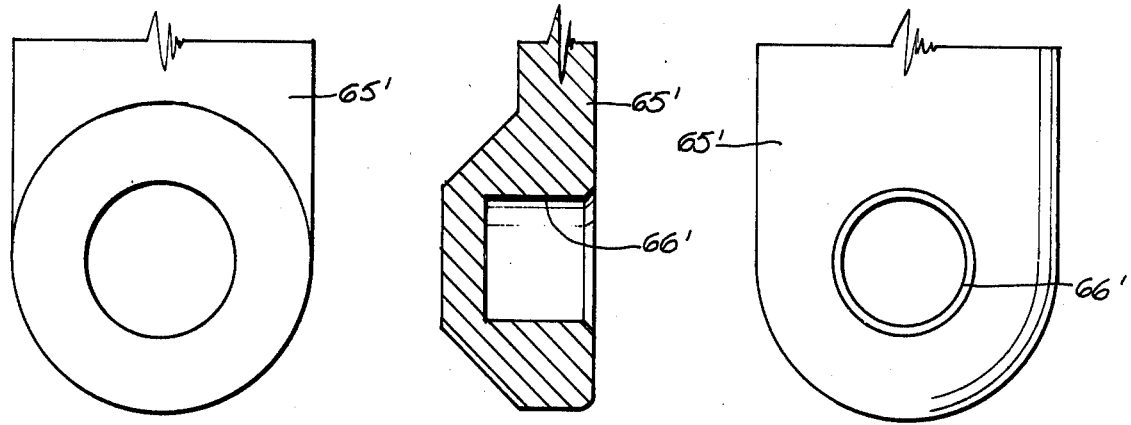
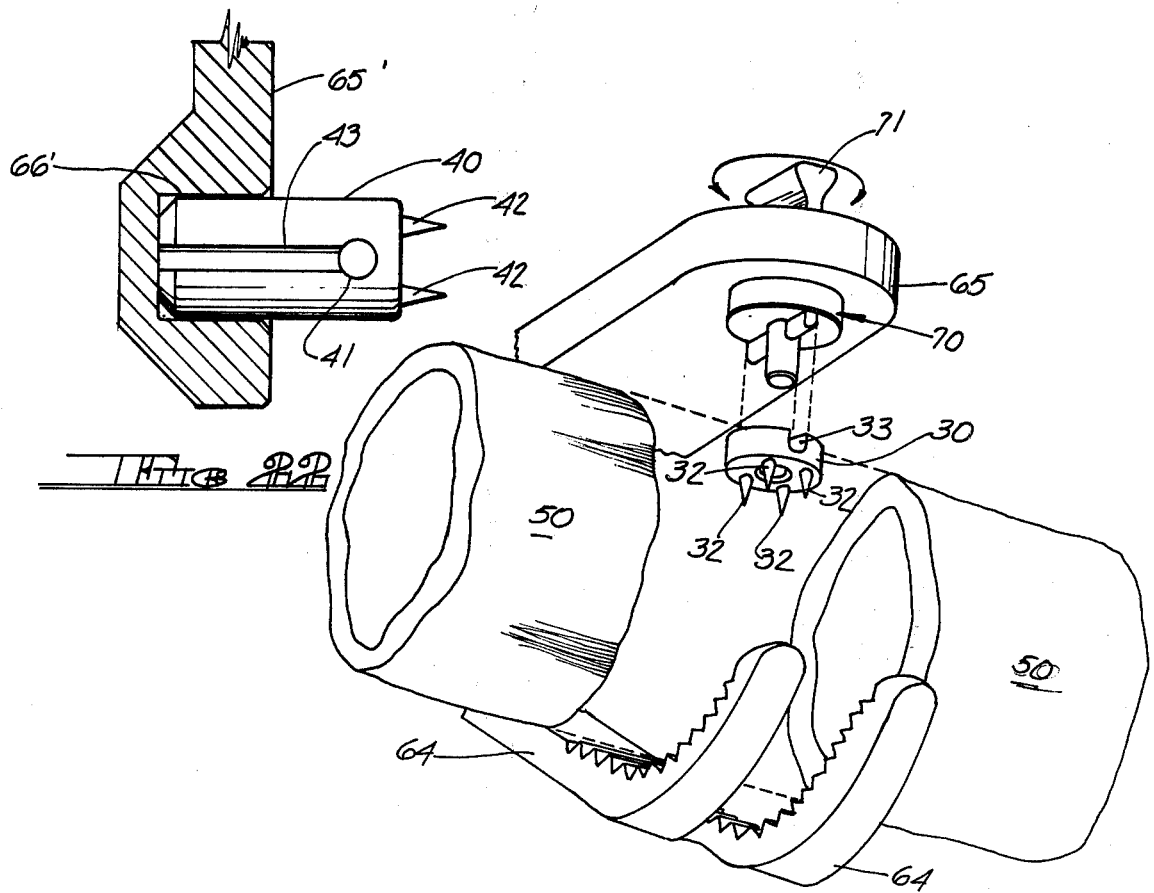

FRACTURE FIXATION BY CERCLAGE UTILIZING CORTICAL BONE TACK AND PULL-OUT TENSION DEVICE

BACKGROUND OF THE INVENTION

1. Field of the Invention

This invention relates to orthopedic implants used in the internal fixation of bone fractures in living human beings and animals, to a method of fracture fixation which preserves the vascular integrity of the cortex and periosteum of the bone structure, and to an applier means for insertion of implants into a fractured bone. While not so limited, the implants of the invention have particular utility in cerclage (circumferential wiring) and hemicerclage wiring in combination with intramedullary pins for fixation of fracture of long bones. The invention provides improvements in the general principles applicable to repair of fractures, viz., anatomical reconstruction, preservation of vascularity, rigid internal fixation, minimum trauma, and early ambulation.

2. Description of the Prior Art

Circumferential wiring for orthopedic procedures in humans and animals has been practiced for a number of years, particularly in the treatment of fractures of the long bones. It has also been used in combination with intramedullary pinning. However, problems have been encountered, including fracture non-union becuase of impairment of circulation or poor fixation, and resorption of bone under the wire.

When simple cerclage or bone bands are used conventionally for immobilization and stabilization of fractures, the wire or band frequently must be removed within several months after installation in order to avoid ring-like sequestrum. This removal requires additional surgery, and if removal is not affected within the appropriate time a new fracture may appear in the area of the sequestra, thus incurring secondary complications.

U.S. Pat. No. 887,074, issued to DePage, discloses a surgical screw bolt having a wire connected to it, the wire being provided to aid in drawing the bolt through an opening.

Plates, screws, pins and the like for fixation of complex bone fractures, are disclosed in U.S. Pat. Nos. 3,477,429; 3,469,573; 3,463,148; 3,334,624; 3,111,945 and 2,602,445.

The use of such devices generally involve removal thereof from the bone after union by additional surgery, which was often major.

It is therefore evident that a genuine need exists for orthopedic devices and a method for the internal fixation of bone fractures which avoids the above problems and which will permit the use of multiple full cerclage wires or hemicerclage wires either with or without intramedullary pinning.

SUMMARY OF THE INVENTION

It is a principal object of the invention to provide orthopedic implants for the internal fixation of bone fractures by wire which overcomes or avoids the above problems by preventing migration of the wire and reducing the area of pressurized contact between the wire and bone.

It is a further object of the invention to provide a method of fixation of a bone fracture by wire which comprises inserting implants which elevate the wire from the bone at intervals, thereby preserving the vascular integrity of the cortex and periosteum of the bone and avoiding bone resorption.

It is still another object of the invention to provide applier means for attachment of orthopedic implants.

According to the invention there is provided an orthopedic implant comprising a cylindrical body portion having a circular bore therethrough through which a wire may be passed, a plurality of pointed pins at one end of the body portion adapted to be embedded in the cortex of a bone adjacent the fracture site, and at least one groove on the surface of said body portion in which a wire may be accommodated whereby to prevent movement of said wire after tightening thereof.

In a preferred embodiment the orthopedic implant of the present invention comprises an austenitic stainless steel cylindrical body portion having at one end thereof four sharp points of martensitic stainless steel, a circular axial bore therethrough, and a diametrical groove across the end of said cylindrical body portion remote from said points.

In another preferred embodiment an orthopedic implant of the invention comprises a cylindrical body portion of austenitic stainless steel having at one end thereof four sharp points of martensitic stainless steel, a diametrical circular bore through said body portion adjacent said one end, and two longitudinal grooves on opposite sides of said body portion in alignment with the openings of said bore.

The method according to the present invention comprises embedding at least one implant of the type defined above in the cortex of a fractured bone adjacent the fracture site, encircling the fractured bone with a stainless steel wire, positioning the wire in a groove in the implant, and tightening the wire by twisting.

In a preferred embodiment the orthopedic implant is embedded by means of an applier means which exerts constant pressure on the implant until the points thereof are buried in the bone cortex.

BRIEF DESCRIPTION OF THE DRAWINGS

Reference is made to the accompanying drawing wherein:

FIG. 1 is a perspective view illustrating fixation of a long bone fracture by means of an intramedullary pin and three cortical bone tacks of the invention;

FIG. 2 is a top plan view of a cortical bone tack in accordance with the invention;

FIG. 3 is a side elevation of the cortical bone tack of FIG. 2;

FIG. 4 is a sectional view taken on the line 4—4 of of FIG. 2;

FIG. 5 is a bottom plan view of the cortical bone tack of FIG. 2;

FIG. 6 is a perspective view illustrating fixation of a long bone fracture by means of an intermedullary pin, two cortical bone tacks and a pull-out tension post according to the invention;

FIG. 7 is a bottom plan view of a pull-out tension post of the invention;

FIG. 8 is a top plan view of the tension post of FIG. 7;

FIG. 9 is a side elevation, partially in section, of the tension post of FIG. 7;

FIG. 10 is a perspective view illustrating fixation of a long bone fracture by means of double hemicerclage with four cortical bone tacks of the invention wherein an axial bore in two of the bone tacks is used as the sole fixation;

FIGS. 11-22 are plan views, partially in section, illustrating an applier means in accordance with the invention for insertion of a cortical bone tack and a pull-out tension post into a fractured bone; and FIG. 23 is a perspective view illustrating embedding of a cortical bone tack by means of the applier means of FIGS. 11-22.

DESCRIPTION OF THE PREFERRED EMBODIMENTS

Referring to the drawings, one embodiment of an orthopedic implant is shown in FIGS. 2-5. A cortical bone tack in accordance with these figures comprises a cylindrical body portion 30 having an axial bore 31 therethrough. Projecting from one end of the body portion are four sharply pointed pins 32 set into bored holes in the body portion and staked, as best seen in FIG. 4. A diametrical groove 33 is formed across the top of body portion 30 remote from the pins 32.

Preferably the pins are set into bored holes 0.10 inch deep and project outwardly 2mm. The pins have a body diameter of 0.035 inch and a taper of 0.093 inch. The height of the cortical tack is variable and dependent on the type of bone to be fixed.

Another embodiment of an orthopedic implant is shown in FIGS. 7-9.

A pull-out tension post in accordance with these figures comprises a cylindrical body portion 40 having a diametral circular bore 41 therethrough adjacent one end thereof. Four sharp pointed pins 42 project from the same end of the body 40 near which the bore 41 is provided. A pair of oppositely disposed longitudinal grooves 43 is formed in the body portion 40. As shown in FIG. 9 these grooves are in alignment with the bore 41. At the end of the body remote from the pins, the grooves are chamfered or tapered inwardly as shown at 43a in FIG. 8.

The pins are set into bored holes and staked as described above with respect to the cortical bone tack of FIGS. 2-5.

In the embodiment of FIGS. 7-9 the pins are set into bored holes 0.10 inch deep, and project outwardly 1.5mm. The pins have a body diameter of 0.040 inch and a taper of 0.078 inch.

The staking operation deforms the body surface around the edge of the bore thereby descreasing the inside diameter and preventing the pin from being pulled out subsequently.

Both the cortical bone tack and pull-out tension post are of stainless steel. The cylindrical body portion is produced by machining an austenitic stainless steel, preferably AISI Type 303 in the annealed condition, comprising, by weight percent, 0.15% maximum carbon, 17.0 to 19.0% chromium, 8.0 to 10.0% nickel, phosphorus, sulfur and selenium each 0.07% minimum, zirconium and molybdenum each 0.60% maximum, and remainder iron. This is a free-machining grade 18-8 austenitic stainless steel.

The pins are polished and heat treated martensitic stainless steel, preferably preferably AISI Type 420 comprising, by weight percent, more than 0.15% carbon, 12.0% to 14.0% chromium, and remainder iron.

After final assembly the implants should be passivated in a conventional acid and/or acid salt solution in order to remove contaminating iron particles and produce a passive film on the steel surfaces. A passivating treatment which is suitable for both austenitic and martensitic stainless steels in a 20% nitric acid and 2% sodium dichromate solution in which the parts are immersed at 110°-120° F. for 15 to 20 minutes. Thereafter the parts are washed in water and dried.

The carbon contents of metals used in medical implants has been found to be significant, and the preferred Type 303 and Type 420 stainless steels have carbon contens which are appropriate for this purpose, as well as the desired physical properties.

Different types of arrangements which may be used involving the implants of the present invention are shown in FIGS. 1, 6 and 10.

Referring to FIG. 1 there is shown fixation of a long bone fracture by means of an intramedullary pin, three cortical bone tacks and a single cerclage wire, by way of exemplary embodiment. The fractured bone is shown generally at 50, and an intramedullary pin is shown at 51. After the cortical bone tacks 30-33 are embedded in the cortex of the bone, in a manner described hereinafter, a stainless steel monofilament surgical grade wire of conventional type indicated at 55 in FIG. 1 is wrapped around the bone and positioned in the groove 33 in the top of each of the bone tacks. The wire loop is then tightened fully and thereafter twisted as shown at 55a. Preferably a wire tightener-twister incorporating a tension gauge is used, such as a Rhinelander Wire Tightener-Twister, produced by Richards Manufacturing Company, Inc., of Memphis, Tenn.

Referring to FIG. 6, fixation of a long bone fracture is shown wherein two cortical bone tacks and a pull-out tension post are used in combination with an intramedullary pin and cerclage wire. After embedding the two cortical bone tacks 30-33 a monofilament stainless steel wire 55 is passed around the bone and engaged in the grooves 33 on the outwardly facing surfaces of the two cortical bone tacks. The pull-out tension post 40-43 is then embedded, and the free ends of the wire are passed in opposite directions through the diametrical bore 41 of the pull-out tension post. Each free end is then bent upwardly and engaged in a longitudinal groove 43 on opposite sides of body portion 40, followed by tightening and twisting, as indicated at 55a, in the same manner explained above.

In the embodiment of FIG. 6 the tension post and wire would be removed after healing, while the cortical bone tacks could remain permanently embedded in the bone. Depending upon the anatomical location, the tension post may either be externalized or sutured over. In the latter case removal requires only a small skin incision.

Referring next to FIG. 10, fixation of a long bone fracture is shown by means of double hemicerclage wiring with four cortical bone tacks in accordance with the invention, and no intramedullary pin. In this procedure a wire 55 is passed through an axial bore 31 in the lower-most cortical tack as shown in FIG. 10, upwardly through holes drilled in the bone 50, then upwardly through bore 31 in a tack positioned substantially opposite the lowermost tack and bent into engagement with groove 33 therein. The other free end of wire 55 is brought around the outside of the bone, engaging groove 33 in the tack shown on the left-hand side of the bone in FIG. 10, the wire then being tightened and twisted as shown at 55a, in the manner explained above. A second hemicerclage wire 56 is then applied in the same manner by passage through bore 31 in the lowermost tack and bore 31 in the uppermost tack, followed by tightening and twisting as shown at 56a in the same manner. It will be noted that the wires are stabilized by engagement in grooves 33 in all the tacks. Hence, no wire migration occurs.

It is believed that the above exemplary methods show the verstility of the present invention. The cortical tacks and/or pull-out tension posts may be used in cerclage or hemicerclage wiring, with or without an intramedullary pin for fixation of a long bone fracture in a variety of ways. In most cases multiple wire loops should be used rather than fixation by one wire loop alone. The wires should be placed no less than 1cm apart and should be within about 0.5cm of the lip of each oblique fracture fragment.

The grooves across the outwardly facing tops of the cortical tacks are of sufficient size to accept one 1.2mm cerclage wire or two 0.77mm wires. When using a pull-out tension post in combination with cortical tacks, it is preferred to embed the tension post after the cortical tacks and cerclage wire are in place.

Other applications for the implants and method of the invention include fixation of fractures by hemicerclage wiring and intramedullary pinning using opposing cortical bone tacks or a pull-out tension post opposite a cortical bone tack; fixation of onlay and inlay bone grafts with cortical bone tacks and cerclage wire; and fixation of fracture fragments by hemicerclage wiring using cortical bone tacks and/or a pull-out tension post.

The size of the implants can of course be varied so as to be appropriate to the particular bone fracture. With such size modifications the invention is applicable to fractures of displacements involving short bones, sesamoid bones, flat bones and irregular bones.

Referring to FIGS. 11–22, applier means having particular utility for embedding the cortical bone tack and pull-out tension post of the present invention in the cortex of a bone is indicated generally at 60. This means comprises a forceps having conventional handles 61, 62, a pivot post 63, a lower bifurcated curved and serrated jaw 64 and an upper, substantially planar jaw 65. The upper jaw 65 is provided with a stepped circular bore 66 in the embodiment of FIGS. 15–18 which accomodates a male slip joint indicated generally at 70. The male slip joint is configured in such manner as to mate with the axial bore 31 and groove 33 of a cortical bone tack so as to secure it against rotation or movement when pressure is applied thereto. A desired position of adjustment may be selected prior to applying pressure, as shown in FIG. 15 by rotation of an upwardly extending shoulder 71. The manner of operation is shown schematically in FIG. 23.

In the embodiment of FIGS. 19–22, an upper jaw 65' is shown which is adapted to embed a tension pull-out post of the invention. Jaw 65' is provided with a circular recess 66' of constant diameter which accommodates a tension pull-out post as shown in FIG. 22. The manner of operation is substantially the same as that shown in FIG. 23. It will be understood that no means for rotational adjustment of the pull-out tension post is needed in the embodiment of FIGS. 19–22 since the post when seated in the recess 66' projects outwardly a sufficient distance to permit adjustment by direct rotation of the post itself.

Tests have been conducted by introducing the implants of the invention into a dog and a cat. In each animal a lateral approach was made to the shaft of the femur. A long oblique fracture was created surgically with a nitrogen powered drill and an osteotome. The fracture was distracted in each animal, and radiographs were taken. In the cat the fracture was then repaired by insertion of a Kirschner intramedullary pin of 3.97mm diameter, a proximal cerclage wire of 0.50mm diameter positioned over a single cortical tack, and a distal cerclage wire of 0.50mm diameter attached to a single pull-out tension post. The fracture was repaired in the dog by means of a Kirschner intramedullary pin of 4.76mm diameter, a proximal cerclage wire of 0.63mm diameter encircling a single cortical tack, and a distal cerclage wire of 0.77mm diameter attached to a single pull-out tension post. In each animal the fascia was closed with 2-0 medium chromic gut and the skin closed with 2-0 Vetafil, sold by S. Jackson Inc., Washington, D.C. In the cat the tension post was satured over, whereas the tension post was externalized in the dog. The pull-out tension post was removed along with the distal cerclage wire 28 days postoperatively in the cat and 21 days postoperatively in the dog. The proximal cerclage wire and cortical tack were not removed from the cat or the dog, being left in place for long term studies. Posteroanterior and lateral radiographs were taken at appropriate intervals.

The Kirschner intramedullary pin was removed from the cat after 8 weeks and from the dog after 7 weeks.

The pull-out tension posts were tolerated by both animals even when externalized outside the skin to facilitate simple removal (in the dog). Twelve months after repair of the fractures, the remaining cortical tacks and proximal cerclage wires continued to be accepted. Neither animal has shown by sign of lameness.

These tests on the dog and cat have thus shown that the implants of the present invention are readily accepted and that multiple full cerclage wires can be used in combination with an intramedullary pin as additional fixation in oblique fractures of long bones. The tests were conducted on fixation of oblique fractures of the femur because the system is required to withstand greater forces here than anywhere else in the skeleton.

Subsequently the implants and method of the invention were used in a six month old female mixed breed dog weighing 45 pounds, which had been hit by a car. The right rear leg has sustained an avulsion of the tibiotarsal joint, and the left rear leg had sustained a long oblique fracture of the femur.

The avulsed right rear leg was repaired by means of tenorrhaphy and tetrahagonal Z-plasty. The long oblique fracture of the left femur was fixed by cerclage and cortical bone tacks in combination with a threaded Kirshner intramedullary pin. A Kirschner pin of 3.97mm diameter was introduced from the fracture site and driven proximally out the trochanter major. It was subsequently threaded into the distal fragment.

Temporary cerclage wires of 0.63mm diameter were applied to reduce the fracture. Three cerclage wires of 0.77mm diameter were then placed, with each wire encircling a single cortical bone tack, each of which was positioned and embedded to compress the fracture further. Upon tightening and twisting of the wires around the cortical bone tacks, the temporary cerclage wires became very loose and were removed. The fascia was satured with 3-0 chromic gut, and the skin was sutured with 0.30mm Vetafil.

The polytraumatized dog was able to bear weight on both rear legs the morning after surgery. Radiographs taken at appropriate intervals showed primary bone union, including growth over all three cerclage wires, with no indications of bone necrosis from wire migration. The Kirschner pin was removed six weeks after the operation. Examination six months after surgery revealed no signs of lameness or implant rejection.

It is evident from the above description that the present invention provides stable fixation of fractures by multiple cerclage and permits removal of an implant along with its cerclage wire by a simple skin incision. It is further evident that the cortical bone tacks of the invention need not be removed although the pull-out tension posts will always be removed at an appropriate time.

The method of the invention is simpler in application than the conventional repair of fractures of a type which previously required plates. Considerably less trauma results since the procedure of the invention usually requires less exposure of bone, less disturbance of periosteum and periosteal vascular supply, less dissection of muscular attachments, and less time.

Modifications may be made without departing from the spirit and scope of the invention. Thus, although it has been indicated above that the body portions of the cortical bone tack and pull-out tension posts preferably are machined from austenitic stainless steel, it is within the scope of the invention to substitute a synthetic resin which would not be rejected by the body. While four pointed pins are shown in each cortical bone tack and pull-out tension post, the invention is not restricted to a specific number of pins, so long as the number provided insures a stabilized base which secures the cerclage wire and prevents migration thereof. Elevation of the wire from the bone by means of the implants of the invention need not be at specific intervals or entirely around the bone, so long as the vascular integrity of the cortex and/or periosteum is preserved.

The embodiments of the invention in which an exclusive property or privilege is claimed are defined as follows:

1. An orthopedic implant for use in the repair of a bone fracture with wire, comprising a cylindrical body portion having a circular bore therethrough through which a wire may be passed, a plurality of pointed pins at one end of said body portion adapted to be embedded in the cortex of a bone adjacent the fracture site, and at least one groove on the surface of said body portion in which a wire may be accommodated.

2. The implant claimed in claim 1, wherein said cylindrical body portion is formed from an austenitic stainless steel containing a maximum of 0.15% by weight carbon.

3. The implant claimed in claim 1, wherein said pointed pins are formed from a heat treated martensitic stainless steel containing more than 0.15% by weight carbon.

4. The implant claimed in claim 3, wherein four said pointed pins are set and staked in bored holes in said body portion.

5. The implant claimed in claim 1, wherein said circular bore is axial, and wherein said groove is diametral across the end of said body portion remote from said pointed pins.

6. The implant claimed in claim 1, wherein said circular bore is diametral and adjacent said one end of said body portion, and wherein said at least one groove comprises two longitudinal grooves on opposite sides of said body portion in alignment with the openings of said bore.

7. A method of repairing a bone fracture with wire, comprising the steps of embedding a plurality of pointed pins secured to one end of an orthopedic implant in the cortex of a fractured bone adjacent the fracture site, said implant having means for securing said wire against movement after tightening thereof, encircling said bone with said wire adjacent said fracture site, engaging said wire in said securing means in such manner that the wire is elevated out of contact with said bone at the location of said implant, tightening said wire, and twisting the free ends thereof together whereby to avoid bone resorption.

8. The method claimed in claim 7, wherein a plurality of said implants are embedded around said bone adjacent the fracture site, and wherein said wire is engaged in said securing means of each said implant and elevated out of contact with said bone at each location of said implants.

9. The method claimed in claim 8, wherein at least one of said implants is retained permanently in said bone along with said encircling wire.

10. The method claimed in claim 7, wherein said bone is a long bone having a medullary cavity, and including the step of inserting an intramedullary pin into said cavity to extend beyond said fracture site on both sides thereof prior to embedding said orthopedic implant.

11. Apparatus for embedding an orthopedic implant in the cortex of a fractured bone adjacent the fracture site, comprising a forceps having handles, a pivot post, a lower bifurcated, curved and serrated jaw, and an upper substantially planar jaw, said upper jaw having an aperture at least in the inwardly facing surface thereof of a size to accommodate said orthopedic implant and to cause one end of said implant to be pressed against said bone.

12. The apparatus claimed in claim 11, wherein said aperture is a stepped circular bore extending through said upper jaw, and including a male slip joint rotatably secured in said bore, said slip joint having a configuration mating with that portion of said implant in contact therewith.

13. The apparatus claimed in claim 12, including means associated with said slip joint for rotational adjustment of said implant.

14. The apparatus claimed in claim 11, wherein said aperture is a circular recess in said inwardly facing surface of a depth sufficient to accommodate a portion only of said implant, the remainder of said implant projecting outwardly from said jaw a distance sufficient to permit direct manual rotational adjustment thereof.

* * * * *